(12) United States Patent
Rey

(10) Patent No.: US 11,731,822 B2
(45) Date of Patent: Aug. 22, 2023

(54) SYSTEM AND METHOD FOR PACKAGING MEDICAL CONTAINERS

(71) Applicant: A. RAYMOND ET CIE, Grenoble (FR)

(72) Inventor: Gaëtan Rey, Voiron (FR)

(73) Assignee: A. RAYMOND ET CIE, Grenoble (FR)

( * ) Notice: Subject to any disclaimer, the term of this patent is extended or adjusted under 35 U.S.C. 154(b) by 0 days.

(21) Appl. No.: 17/470,935

(22) Filed: Sep. 9, 2021

(65) Prior Publication Data

US 2022/0081179 A1    Mar. 17, 2022

(30) Foreign Application Priority Data

Sep. 11, 2020   (FR) ...................................... 2009217

(51) Int. Cl.
| | |
|---|---|
| *A61B 50/33* | (2016.01) |
| *B65D 77/00* | (2006.01) |
| *B65B 5/06* | (2006.01) |
| *B65B 7/28* | (2006.01) |
| *B65B 31/00* | (2006.01) |
| *B65D 25/10* | (2006.01) |

(Continued)

(52) U.S. Cl.
CPC ............ *B65D 77/003* (2013.01); *A61B 50/33* (2016.02); *B65B 5/068* (2013.01); *B65B 7/2842* (2013.01); *B65B 31/00* (2013.01); *B65D 25/108* (2013.01); *B65D 81/2015* (2013.01); *A61B 2050/006* (2016.02); *A61B 2050/3008* (2016.02); *A61B 2050/314* (2016.02)

(58) Field of Classification Search
CPC ........................... B65D 77/003; B65D 25/108; B65D 81/2015; A61B 50/33; A61B 2050/006; A61B 2050/314; A61B 2050/3008; B65B 5/068; B65B 7/2842; B65B 31/00
USPC ......................................................... 206/364
See application file for complete search history.

(56) References Cited

U.S. PATENT DOCUMENTS

| | | | | |
|---|---|---|---|---|
| 6,007,779 | A | | 12/1999 | Lemieux et al. |
| 6,106,783 | A | * | 8/2000 | Gamble .............. B01L 3/50825 422/553 |

(Continued)

FOREIGN PATENT DOCUMENTS

| | | |
|---|---|---|
| CA | 2215561 A1 | 3/1998 |
| DE | 102008046378 A1 | 3/2010 |

(Continued)

OTHER PUBLICATIONS

French Search Report from French Application No. 2009217, dated May 26, 2021, 2 Pages.

*Primary Examiner* — Steven A. Reynolds
(74) *Attorney, Agent, or Firm* — TraskBritt

(57) ABSTRACT

A packaging system for medical containers having a main opening, comprising: a vessel having a shoulder; a tray provided with cavities that is intended for receiving a medical container and rests on the shoulder; a plurality of caps that close the main opening; and a lid that seals the vessel. A method for packaging medical containers, comprises the following steps: providing a vessel; arranging a tray on the shoulder of the vessel; arranging medical containers in the cavities; arranging a cap on the medical containers so as to close the main opening thereof; sealing a lid on an upper edge of the peripheral wall of the vessel; and placing the vessel in at least one sealed bag.

13 Claims, 3 Drawing Sheets

(51) Int. Cl.
 *B65D 81/20* (2006.01)
 *A61B 50/00* (2016.01)
 *A61B 50/30* (2016.01)

(56) References Cited

U.S. PATENT DOCUMENTS

| | | | | |
|---|---|---|---|---|
| 6,164,044 | A * | 12/2000 | Porfano | A61M 5/344 53/489 |
| 6,939,513 | B2 * | 9/2005 | Berray | B01L 3/50853 220/255 |
| 7,060,226 | B1 * | 6/2006 | Jessop | B01L 9/543 422/526 |
| 7,303,073 | B2 * | 12/2007 | Raynal-Olive | A61L 2/208 422/26 |
| 8,460,622 | B2 * | 6/2013 | Motadel | B01L 3/0275 422/526 |
| D700,712 | S * | 3/2014 | May | D24/224 |
| 9,718,583 | B2 * | 8/2017 | Nicoletti | B65D 65/02 |
| 10,973,939 | B2 * | 4/2021 | McLaughlin | B65B 3/003 |
| 2013/0186793 | A1 * | 7/2013 | Gagnieux | A61M 5/002 206/364 |
| 2014/0374414 | A1 | 12/2014 | Lanier et al. | |
| 2015/0183541 | A1 * | 7/2015 | Deutschle | B65D 77/0446 206/439 |
| 2015/0190566 | A1 * | 7/2015 | Okihara | A61M 5/3134 206/365 |
| 2015/0306259 | A1 * | 10/2015 | Deutschle | B65D 33/25 206/439 |
| 2020/0130894 | A1 * | 4/2020 | Kusogullari | B65D 77/2024 |

FOREIGN PATENT DOCUMENTS

| | | |
|---|---|---|
| EP | 0790063 B1 | 10/2002 |
| EP | 2567905 A1 | 3/2013 |
| WO | 02/40064 A1 | 5/2002 |

\* cited by examiner

SYSTEM AND METHOD FOR PACKAGING MEDICAL CONTAINERS

CROSS-REFERENCE TO RELATED APPLICATION

Pursuant to 35 U.S.C. § 119(a), this application claims the benefit of the filing date of French Patent Application Serial No. 2009217, filed Sep. 11, 2020, for "SYSTEM AND METHOD FOR PACKAGING MEDICAL CONTAINERS," the disclosure of which is hereby incorporated herein in its entirety by this reference.

TECHNICAL FIELD

The present disclosure relates to a packaging system and method for packaging and dispensing medical containers. The present disclosure relates more particularly to the packaging of medical syringes and pharmaceutical vials, with a view to their distribution.

BACKGROUND

As is well known per se, syringes are medical devices intended to contain a medical solution that will subsequently be administered to a patient. Syringes are typically formed of an elongated cylindrical body that is configured to receive the medical solution.

As discussed in EP0790063, a common approach to packaging syringes is shown in FIG. 1. This packaging system comprises a vessel 10 in which a tray 20 is arranged that is provided with individual cavities 21 each intended to accommodate the tubular body of a syringe 50, a lid 40 sealing the vessel 10 and a bag surrounding the assembly. This packaging system also comprises a foam sheet 30 arranged over the syringes.

In order for the syringe to be supplied in a condition that is compatible with medical use, particular care must be taken in its packaging. It is particularly desirable to avoid the risks of contamination, in particular particulate, to prevent foreign bodies from being injected into the body of a patient. This objective is not achieved by the current packaging system shown in FIG. 1. In fact, during the packaging/unpacking and transport of the syringes, the foam sheet may generate particles by friction that are liable to contaminate the syringes. Particles initially present in the packaging system are also liable to contaminate the syringes by entering the space between the sheet and the syringes. In addition, when the lid is removed, the latter generates a significant quantity of particles, which are deposited on the sheet. During the subsequent removal of this sheet, the particles that have been deposited therein may fall out and are then liable to contaminate the syringes.

BRIEF SUMMARY

An aim of the present disclosure is to provide a packaging system and method that differ from and improve on the prior art. More particularly, an aim of the present disclosure is to provide a packaging system as well as a packaging method limiting the introduction of particles into medical containers, in particular during their packaging/unpacking and their transport.

With a view to achieving this aim, the object of the present disclosure proposes a packaging system for medical containers provided with a main opening comprising:

a vessel having an opening, a bottom and a peripheral wall, the peripheral wall having a shoulder;

a tray placed in the vessel and resting on the shoulder, the tray being provided with a plurality of cavities each comprising a single medical container;

a plurality of caps, each cap being placed on a medical container to close the main opening thereof;

a lid sealed on the upper edge of the peripheral wall of the vessel in order to close it.

According to other advantageous and non-limiting features of the present disclosure, taken alone or in any technically feasible combination:

the plurality of caps is arranged on a lower face of a cover;
    the cover is a plate;
    the cover comprises a plurality of strips;
    the strips and the caps are made of a flexible material;
    each strip comprises bending regions formed between each cap;
    the lid is porous;
    the vessel is placed, under vacuum, in at least one sealed bag.

According to yet another aspect, the object of the present disclosure proposes a method of packaging medical containers provided with a main opening, wherein the method comprises the following steps:

providing a vessel having an opening, a bottom and a peripheral wall, the peripheral wall having a shoulder;

arranging a tray in the vessel, the tray being provided with a plurality of cavities and resting partially on the shoulder;

arranging medical containers in at least some of the cavities;

respectively arranging a plurality of caps on the medical containers so as to close the main opening thereof;

sealing a lid on an upper edge of the peripheral wall of the vessel.

According to other advantageous and non-limiting features of the present disclosure, taken alone or in any technically feasible combination:

the lid is secured to the vessel by welding the lid to the upper edge of the peripheral wall of the vessel;
    the lid is also sealed to the caps;
    the step of arranging the plurality of caps comprises arranging a cover on the medical containers, the caps being arranged on a lower face of the cover;
    the lid is also sealed to the cover;
    the packaging method comprises, after the lid has been sealed on the vessel, a step of placing the vessel in at least one sealed bag and evacuating all air from the bag.

BRIEF DESCRIPTION OF THE FIGURES

Other features and advantages of the present disclosure will become apparent from the following detailed description of Embodiments of the present disclosure, which is provided with reference to the accompanying drawings, in which.

DETAILED DESCRIPTION OF THE INVENTION

General Description of the Packaging System

Figure 1:
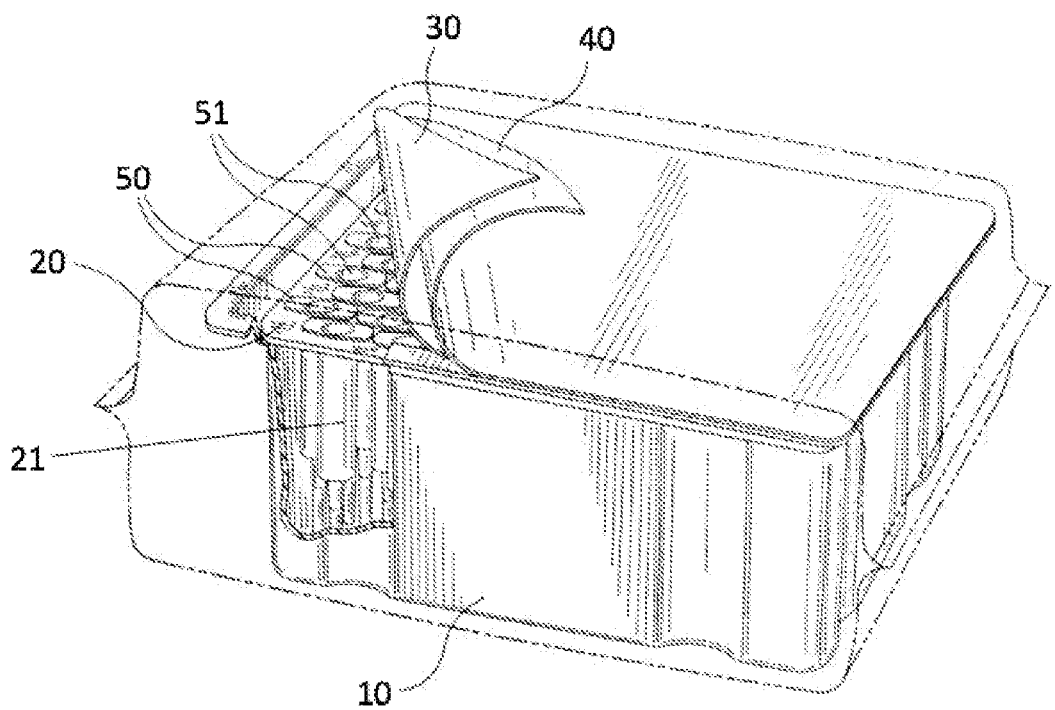
FIG. 1 shows a packaging system according to the state of the art.
Figure 2:
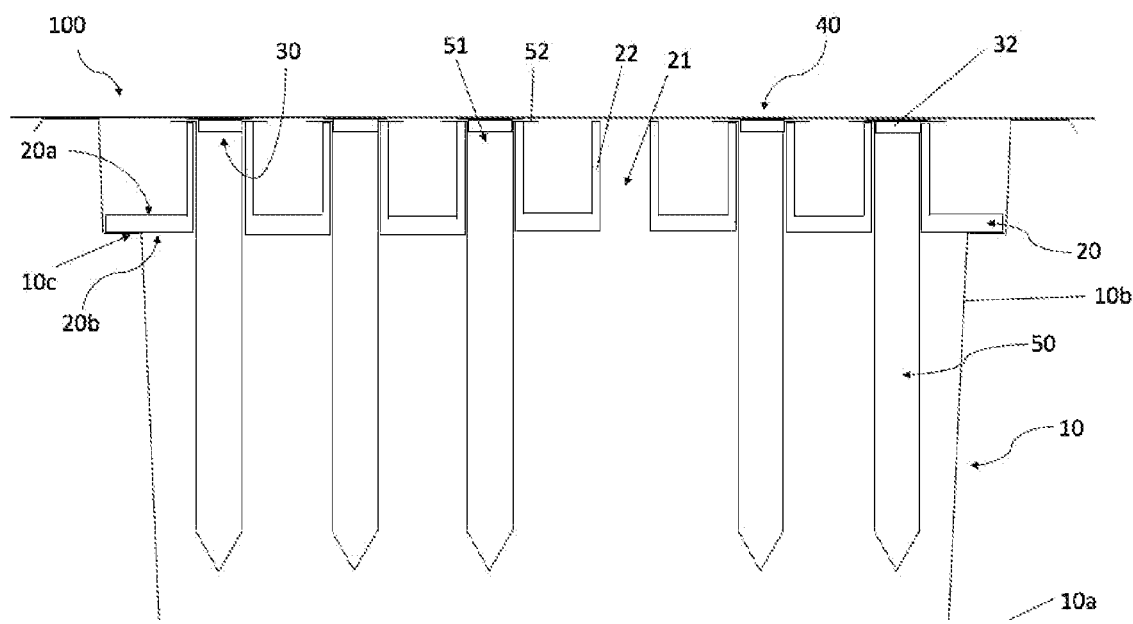
FIG. 2 shows a packaging system according to the present disclosure.

As shown in FIG. 2, a packaging system 100 according to the present disclosure comprises a vessel 10, a tray 20 provided with cavities 21, caps 32 (which will be able to be borne by a cover 30, as will be explained in the remainder of the description), and a lid 40 arranged on the opening of the vessel 10 in order to close it. The vessel 10 containing the tray 20, and closed by the lid 40, is intended to be placed in at least one airtight bag (and generally two of these bags).

The tray 20 accommodates a plurality of medical containers 50 stored individually in one of the cavities 21 of the tray 20 without any contact being possible between them. The term "medical containers 50" denotes any type of container for medical use that must remain sterile and/or clean and free from any particulate contamination. In the examples described and shown, these are syringes, but they could just as easily be any other type of medical container, such as vials, collection tubes, etc. The medical containers 50 are provided with a main opening 51 providing access to the interior of the container 50. The main opening 51 can be surrounded by a flange 52 that can be taken advantage of to retain the container in its cavity. The shape and volume of the cavities 21 will of course be adapted such that they can accommodate the medical container 50 in question.

Description of the Vessel

The vessel 10 is a hollow packaging element intended to receive the tray 20 in which the medical containers 50 are placed. The vessel 10 comprises an opening, a bottom 10a and a peripheral wall 10b that delimits its general shape. The peripheral wall 10b is provided with a shoulder 10c allowing the handling of the vessel 10, in particular by automated equipment, as well as the maintenance of the tray 20, the latter bearing on the shoulder 10c when it is placed in the vessel 10. Advantageously, the vessel 10 has a parallelepipedal shape in order to optimize the space required for storing a given number of medical containers 50. The dimensions of the vessel 10 are chosen depending on the number of medical containers 50 to be packaged. These dimensions may comply with a norm or a standard so as to facilitate use on an industrial scale. The vessel 10 may be formed from a plastic material, for example polypropylene, amorphous polyethylene terephthalate or a styrenic polymer such as polystyrene.

Description of the Tray

The tray 20 is provided with a plurality of cavities 21 and comprises an upper face 20a as well as a lower face 20b. The cavities 21 are typically arranged in rows on the tray 20 and can be of various types.

In their simplest form, the cavities 21 are constituted by openings formed on the tray 20. Medical containers 50 (e.g. syringes) are inserted through the openings until the flange 52 of the medical containers 50 abuts against the edge of the opening to retain the medical containers 50 assembled to the tray 20. Optionally, as shown in FIG. 2, the openings of the tray 20 can be delimited, on the side of the upper face 20a of the tray 20, by walls 22 to form the cavities 21. These walls 22 make it possible to relocate the stop point between the medical container 50 and the tray 20 in order to place the medical container 50, and therefore its main opening 51, at a given height. This is very particularly advantageous if it is desired to have the main opening 51 of the medical containers 50 in a plane close to that formed by the upper edges of the vessel 10.

Of course, other forms of cavity 21 can also be envisaged, such as a simple cavity provided with a bottom on which the medical container 50 can rest. This is particularly advantageous when the latter does not have a stop element able to limit its insertion through an opening.

The trays can be made of a plastic material, for example based on polypropylene, polyoxymethylene or styrenic polymer of the PS type.

Description of the Cover

The term "cover 30" generally denotes any element placed in the vessel 10 on the medical containers 50 to close their main opening 51.

According to a first embodiment, the cover 30 can be a plate 30 provided on its lower face with a plurality of caps 32 able to close the main opening 51 of the medical containers 50, for example by interlocking. The plate 30 can have dimensions similar to that of the tray 20. Advantageously, this plate 30 is flexible.

Figure 3A:
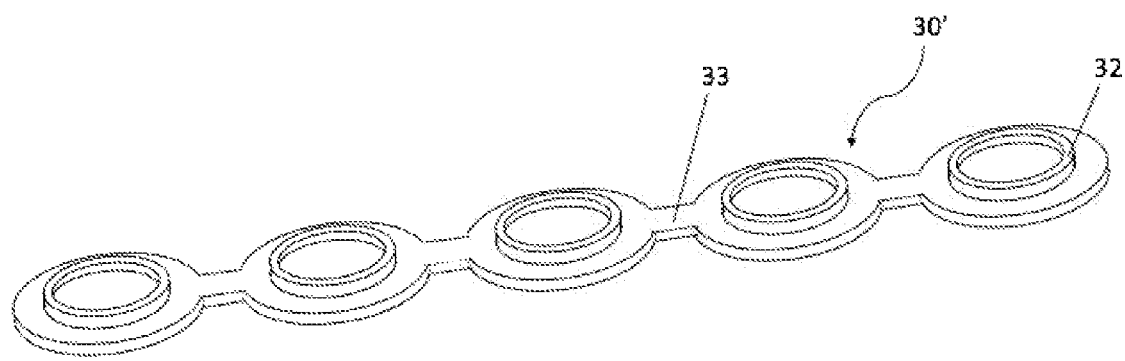
FIGS. 3a and 3b respectively show a cover according to a second and a third embodiment of the present disclosure.
Figure 4A:
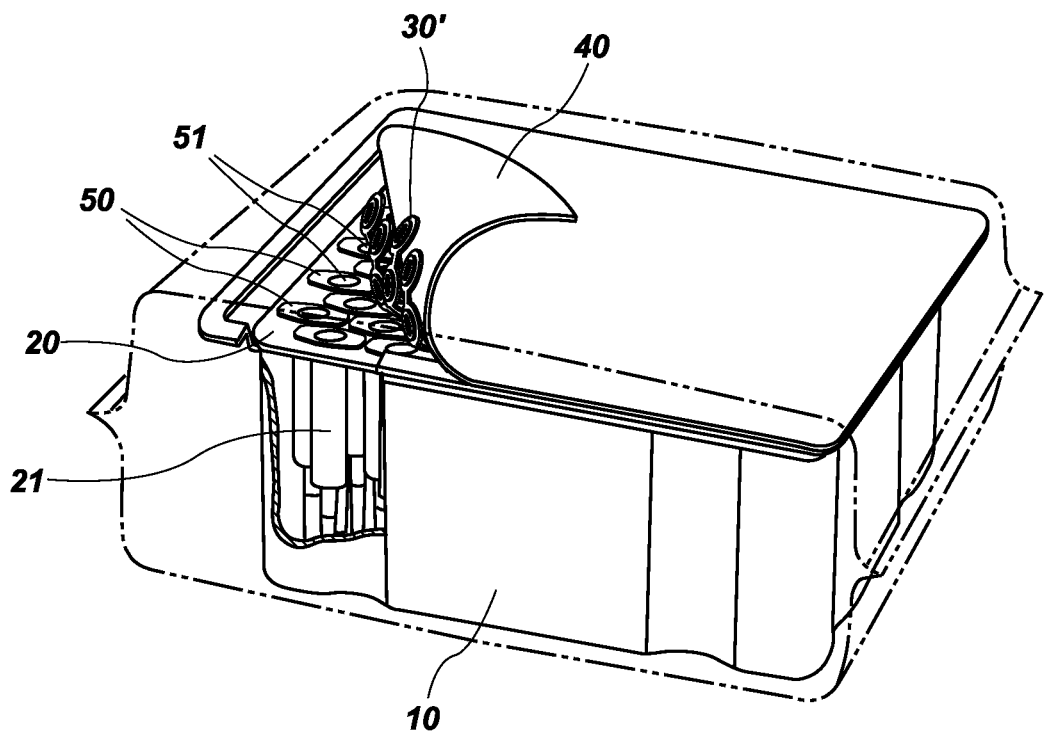
FIG. 4a shows a packaging system according to one example of the present disclosure.

According to a second embodiment, illustrated in FIGS. 3a and 4a, the cover comprises a plurality of individual strips 30' intended to cover and respectively close rows of medical containers 50 arranged in the cavities 21 of the tray 20. These strips 30' can be rigid or flexible. To impart or improve the flexible nature of a strip 30', the latter can be formed by relatively narrow bending regions 33, interconnecting relatively wide support regions bearing the caps 32. The strip 30' and the caps 32 can be formed by a flexible material, for example based on thermoplastic elastomers.

Figure 3B:
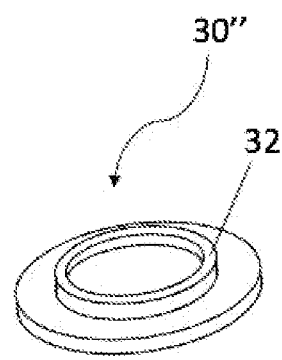
Figure 4B:
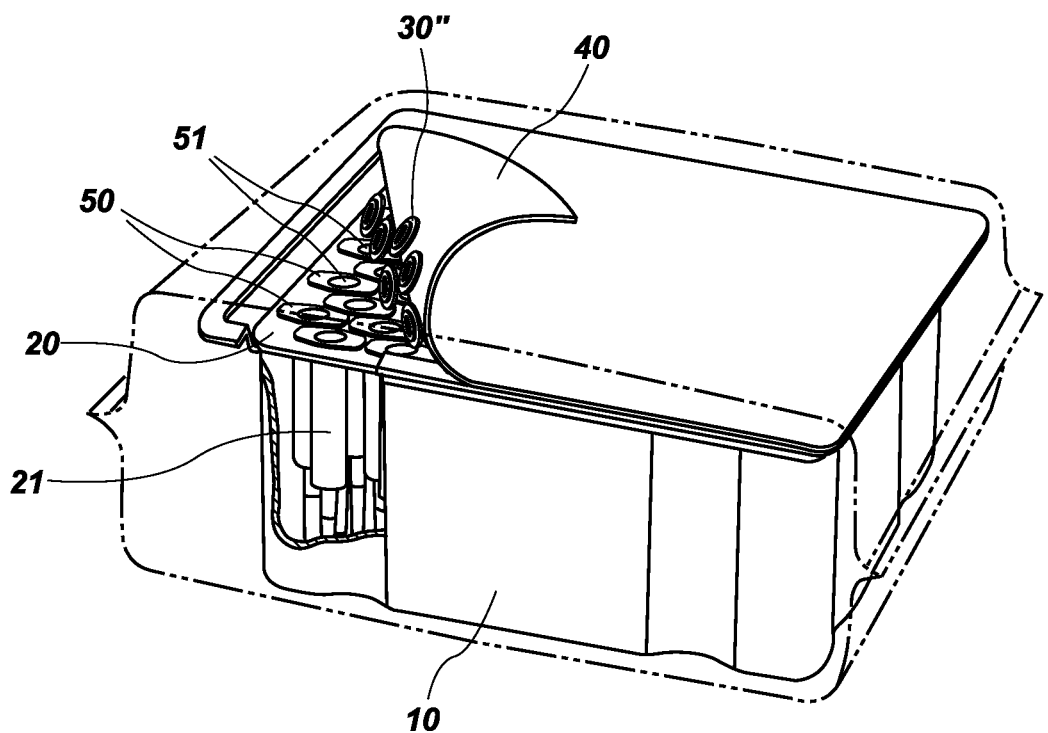
FIG. 4b shows a packaging system according to one example of the present disclosure.

According to a third embodiment, illustrated by FIGS. 2, 3b, and 4b, provision can be made for the cover 30" to be implemented by a plurality of unitary caps 32, these caps being respectively arranged on the medical containers 50 in order to close their main opening 51. They can be soft or rigid caps.

In the second and third embodiment, as well as the first embodiment when the cover 30 is a flexible plate, the covers 30, 30', and 30" are intended to be secured to the lid 40, for example by welding, so that removing the lid 40 (when opening the packaging system 100) naturally causes the opening of the main openings 51 of the medical containers 50, so that the user can directly access the containers without requiring an additional step.

In the case where the strips are rigid, they are preferably arranged perpendicular to the direction of removal of the porous lid 40 in order to facilitate its removal. If the strips 30' are flexible enough, they can be arranged without any particular orientation with respect to the opening direction of the lid 40.

The caps 32 make it possible to individually close the main opening 51 of the medical containers 50, thus preventing particles from entering the medical containers 50 to contaminate them, during the packaging/unpacking and transport of the medical containers 50.

Description of the Lid

The lid 40 is intended to be sealed, for example by means of plastic welding, on the upper edges of the peripheral wall 10b of the vessel 10 as well as to the cover 30, once the vessel 10 has been filled with the tray 20 carrying the medical containers 50 and the cover 30. The lid 40 is intended to keep the medical containers 50 clean and to prevent particles from entering the vessel 10.

Advantageously, the lid 40 is sealed to the cover 30 simultaneously with its sealing to the upper edges of the peripheral wall 10b of the vessel 10.

To allow this, the elements of the packaging system 100 are dimensioned so that the exposed surface of the cover 30, when the latter is arranged on the medical containers 50, is flush with the upper edge of the wall of the vessel 10.

Optionally, the lid 40 is porous to allow a vacuum step; the porosity to the air of the lid 40 makes it possible to extract the air from the vessel. It may for example be made of TYVEK®, a material commonly used in the pharmaceutical industry.

Description of the Packaging Method

In order to minimize contamination by particles and in order to preserve the possible sterility of the medical containers, the various steps described below are preferably carried out in a controlled environment.

The tray 20 is arranged in the vessel 10 so as to rest, at least partially, on the shoulder 20c. Medical containers 50 are then, or were previously, arranged in the cavities 21 of the tray 20.

A cover 30 is placed on the upper face 21a of the tray in order to individually close the openings of the medical containers 50. As has already been mentioned, this cover 30 can be formed by a plate provided with caps 32, which is therefore arranged integrally on the medical containers 50. It may alternatively be a plurality of flexible or rigid strips 30' bearing caps 32, and placed in rows on the tray 20 so as to close the main opening of the medical containers 50, or else individual caps 30" arranged on each medical container 50. Optionally, a combination of these options can be used to close the medical containers.

Alternatively, in particular in the case of individual caps 30" the medical containers 50 can be closed beforehand before being arranged in the vessel 10. This alternative makes it possible to offer additional protection against the particles that may be generated during the packaging and/or handling of the medical containers 50 before placing them in the vessel 10.

The lid 40 is then arranged on the cover 30 and then secured to the upper edges of the peripheral wall 10b of the vessel 10, as well as possibly to the strips 30' when these are present or directly to the caps when the lid 40 is made up of individual caps 32 or even directly to the cover 30 when the latter is a flexible plate.

In a following optional step, the vessel 10, the opening of which has been closed by the lid 40, is placed in at least one airtight bag (and preferably two bags for safety reasons), then is hermetically sealed.

Advantageously, the vacuum is created in this bag before sealing it hermetically. The vacuumization of the assembly allows the movement of the various components of the packaging system 100 to be blocked in order to limit the risk of friction, in particular between the vessel 10 and the tray 20 during transport, and therefore of particle generation. Indeed, during the vacuumization, the lateral walls 10b of the vessel 10 are deformed and press against the edge surface of the tray 20, thus blocking its movement. Vacuumization also makes it possible to individually close each medical container 50 by pressing and holding the caps 32 in place in each main opening 51.

Opening the Packaging System

To open the packaging system and access the medical containers packaged therein, the vessel 10 containing the stack of trays 20 is taken out of the bag first. The lid 40 is then removed to expose the cover 30. The cover 30 is removed from the vessel to expose the medical containers 50. When the cover 30 is sealed to the lid 40, in particular when it is in the form of rigid or flexible strips 30', or individual caps or a flexible plate, opening this lid naturally leads to removing the caps 32 from the medical containers 50, without any additional operation. The medical containers 50 can then be picked up individually or row by row, manually and/or automatically by a machine.

In the case where the cover 30 is not sealed to the lid 40, the cover 30 allows the containers 50 to be opened at the very last moment before filling and offers additional protection against the particles generated during the removal of the lid 40. However, an additional step will be necessary to remove the cover and to be able to fill the medical containers.

Of course, the present disclosure is not limited to the embodiments described and it is possible to add variants without departing from the scope of the invention as defined by the claims.

What is claimed is:

1. A packaging system for medical containers provided with a main opening, comprising:
    a vessel having an opening, a bottom wall and a peripheral wall, the peripheral wall having a shoulder;
    a tray that is removably placed in the vessel and rests on the shoulder, the tray being provided with a plurality of cavities, each of which contains a single medical container;
    a plurality of caps, each cap being arranged on a medical container so as to close the main opening thereof, wherein the plurality of caps is arranged on an underside of a plurality of individual covers, each individual cover taking the form of a strip; and
    a lid sealed on an upper edge of the peripheral wall of the vessel so as to close the vessel.

2. The packaging system of claim 1, wherein the strips and the caps comprise a flexible material.

3. The packaging system of claim 2, wherein each strip comprises bending regions formed between each cap.

4. The packaging system of claim 3, wherein the lid is porous.

5. The packaging system of claim 4, wherein the vessel is placed under vacuum in at least one sealed bag.

6. The packaging system of claim 1, wherein the lid is porous.

7. The packaging system of claim 1, wherein the vessel is placed under vacuum in at least one sealed bag.

8. A method of packaging medical containers provided with a main opening, the method comprising the following steps:
    providing a vessel having an opening, a bottom wall and a peripheral wall, the peripheral wall having a shoulder;
    removably arranging a tray in the vessel, the tray being provided with a plurality of cavities and resting partially on the shoulder;
    arranging medical containers in at least some of the cavities;
    respectively arranging a plurality of caps on the medical containers so as to close the main opening thereof, wherein the step of arranging the plurality of caps includes arranging a plurality of individual covers on the medical containers, the caps being arranged on an underside of the plurality of individual covers, each individual cover taking the form of a strip; and
    sealing a lid on an upper edge of the peripheral wall of the vessel.

9. The packaging method of claim 8, wherein the lid is rigidly connected to the vessel by welding the lid onto the upper edge of the peripheral wall of the vessel.

10. The packaging method of claim 9, wherein the lid is sealed to the cover.

11. The packaging method of claim 10, further comprising, after the lid has been sealed on the vessel, a step of placing the vessel in at least one sealed bag and evacuating the bag.

12. The packaging method of claim 8, wherein the lid is sealed to the cover.

13. The packaging method of claim 8, further comprising, after the lid has been sealed on the vessel, a step of placing the vessel in at least one sealed bag and evacuating the bag.

* * * * *